US010548604B2

(12) United States Patent
Rizzolo

(10) Patent No.: US 10,548,604 B2
(45) Date of Patent: Feb. 4, 2020

(54) SLOW BLOOD VESSEL OCCLUSION APPARATUS

(71) Applicant: Richard A Rizzolo, Ukiah, CA (US)

(72) Inventor: Richard A Rizzolo, Ukiah, CA (US)

( * ) Notice: Subject to any disclaimer, the term of this patent is extended or adjusted under 35 U.S.C. 154(b) by 163 days.

(21) Appl. No.: 15/863,187

(22) Filed: Jan. 5, 2018

(65) Prior Publication Data

US 2019/0209741 A1   Jul. 11, 2019

(51) Int. Cl.
| | | |
|---|---|---|
| *A61B 17/12* | (2006.01) | |
| *A61L 31/10* | (2006.01) | |
| *A61B 17/132* | (2006.01) | |
| *A61L 31/02* | (2006.01) | |
| *A61L 31/04* | (2006.01) | |
| *A61L 31/06* | (2006.01) | |
| *A61B 17/00* | (2006.01) | |

(52) U.S. Cl.
CPC .......... *A61B 17/12* (2013.01); *A61B 17/1325* (2013.01); *A61L 31/022* (2013.01); *A61L 31/048* (2013.01); *A61L 31/06* (2013.01); *A61L 31/10* (2013.01); *A61B 2017/00898* (2013.01); *A61B 2017/00951* (2013.01); *A61B 2017/00964* (2013.01)

(58) Field of Classification Search
CPC ........ A61L 31/06; A61L 31/10; A61L 31/041; A61L 31/048; A61L 31/145; A61L 31/022; A61L 27/18; A61L 27/52; A61B 17/0057; A61B 17/12; A61B 17/12009; A61B 17/12013; A61B 17/1325; A61B 2017/00778; A61B 2017/00893; A61B 2017/00898; A61B 2017/00004; A61B 2017/00597; A61B 2017/12004; A61B 2017/00951; A61B 2017/00964; A61B 5/022233

See application file for complete search history.

(56) References Cited

U.S. PATENT DOCUMENTS

| | | | | |
|---|---|---|---|---|
| 5,509,888 A | * | 4/1996 | Miller | ............ A61B 17/12 128/DIG. 25 |
| 6,171,298 B1 | * | 1/2001 | Matsuura | ............ A61L 17/145 604/891.1 |
| 8,734,318 B2 | * | 5/2014 | Forsell | ............ A61F 2/0036 600/30 |

(Continued)

Primary Examiner — Christopher L Templeton
Assistant Examiner — Mikail A Mannan
(74) Attorney, Agent, or Firm — Donald R. Boys; Central Coast Patent Agency, LLC

(57) ABSTRACT

An occlusion apparatus has a plastic ring with an opening at one point, encased in silicone, with a central opening of a first inside diameter, a silicone bladder in the circular, central opening, providing a hollow, semi-circular silicone ring, a mixture of sodium and potassium salts and polyacrylamide granules at a specific ration of materials enclosed in the silicone bladder, and two stirrups, one affixed on one side and the other opposite the first. The stirrups and the opening provide for spreading the apparatus by the stirrups to place the apparatus over a blood vessel, releasing the apparatus enclosing the blood vessel in the second inside diameter of the bladder, and wherein water passing through walls of the silicone bladder forms a hygroscopic gel that expands over time with further absorption of water, closing the second inside diameter of the silicone bladder, slowly occluding the blood vessel.

6 Claims, 4 Drawing Sheets

(56) References Cited

U.S. PATENT DOCUMENTS

| | | | |
|---|---|---|---|
| 2004/0138684 A1* | 7/2004 | Eton | A61B 17/12 |
| | | | 606/158 |
| 2014/0066967 A1* | 3/2014 | Levy | A61F 5/003 |
| | | | 606/191 |
| 2017/0303928 A1* | 10/2017 | Cazenave | A61B 17/12 |
| 2018/0035994 A1* | 2/2018 | Gharibi Loron | A61B 17/0293 |

* cited by examiner

Section A-A

SLOW BLOOD VESSEL OCCLUSION APPARATUS

BACKGROUND OF THE INVENTION

1. Field of the Invention

The present invention is in the field of medical devices, and pertains more particularly to methods and apparatus for effecting slow occlusion of a blood vessel in treatment of extrahepatic portosystemic shunts affecting small animals.

2. Discussion of the State of the Art

Portosystemic shunts are common congenital vascular anomalies affecting small animals, more particularly, canines and felines patients. Congenital portosystemic shunt (PSS) may be caused by the failure of the fetal circulatory system of the liver to change. Normally, the blood from the placenta bypasses the liver and goes into circulation via the ductus venosus, a blood vessel found in the fetus. A failure of the ductus venosus to close causes an intrahepatic shunt, while extrahepatic shunts are usually a developmental abnormality of the vitelline veins, which connect the portal vein to the caudal vena cava. In animals with PSS, the blood from the intestines only partly goes through the liver, and the rest mixes into general circulation. Therefore, toxins like ammonia are not efficiently cleared by the liver. Most commonly, extrahepatic shunts are found connecting the portal vein or left gastric vein to the caudal vena cava.

The inventor is aware of venous slow-occlusion devices such as the Ameroid constrictor and cellophane band, which are utilized for surgical attenuation of portosystemic shunts. However, these devices work by causing thrombosis and fibrosis (tissue integration) which cannot be reliably controlled over time due to different reactions in different patients.

Therefore, what is clearly needed is a slow-occlusion apparatus for animals that works reliably to close a vessel within and at the culmination of a prescribed time period.

BRIEF SUMMARY OF THE INVENTION

In one embodiment of the invention an occlusion apparatus is provided, comprising a semi-rigid, semi-circular plastic ring, having an opening at one point of circumference, fully encased in silicone material, having an outside diameter and leaving a circular, central opening of a first inside diameter, a silicone bladder formed on the first inside diameter of the circular, central opening, from the open point on the circumference, back to the open point in the circumference, providing a hollow semi-circular silicone ring, leaving a central opening of a second inside diameter, a mixture of sodium and potassium salts and polyacrylamide granules at a specific ration of materials, the mixture fully enclosed in the silicone bladder, and two stirrups, one affixed on one side of the outside diameter of the encased plastic ring, and the other opposite the first along a diameter at a right angle to a diameter passing through the opening at the one point of the circumference of the encased plastic ring. The stirrups and the opening at one point of circumference provide for spreading the apparatus by the stirrups to place the apparatus over a blood vessel, releasing the apparatus enclosing the blood vessel in the second inside diameter of the bladder, and wherein water passing through walls of the silicone bladder forms a hygroscopic gel that expands over time with further absorption of water, closing the second inside diameter of the silicone bladder, slowly occluding the blood vessel.

In one embodiment of the apparatus ratios of materials in the silicone bladder are controlled to cause the bladder to fully occlude a blood vessel in a time period of about six weeks. Also in one embodiment the stirrups are formed of a fabric material, coated fully in silicone, and are mounted to the encased plastic ring by a silicone adhesive. Also in on embodiment the plastic ring is formed of medical grade polyetheretherketone (PEEK), and has a rectangular cross section. In one embodiment the first inside diameter is about 5 millimeters, and in one embodiment the bladder is joined to the inside diameter of the encased plastic ring by a silicone adhesive. Also in one embodiment In another aspect of the invention a method for occluding a blood vessel is provided, comprising steps of spreading an occlusion apparatus comprising a semi-rigid, semi-circular plastic ring, having an opening at one point of circumference, fully encased in silicone material, having an outside diameter and leaving a circular, central opening of a first inside diameter, a silicone bladder formed on the first inside diameter of the circular, central opening, from the open point on the circumference, back to the open point in the circumference, providing a hollow semi-circular silicone ring, leaving a central opening of a second inside diameter, a mixture of sodium and potassium salts and polyacrylamide granules at a specific ration of materials, the mixture fully enclosed in the silicone bladder, and two stirrups, one affixed on one side of the outside diameter of the encased plastic ring, and the other opposite the first along a diameter at a right angle to a diameter passing through the opening at the one point of the circumference of the encased plastic ring, by the stirrups, placing the apparatus over the blood vessel to be occluded, such that the blood vessel is surrounded by the bladder, and releasing the apparatus. Water passing through walls of the silicone bladder by osmosis forms a hygroscopic gel with the mixture of salts and polymer, that expands over time with further absorption of water, closing the second inside diameter of the silicone bladder, slowly occluding the blood vessel.

In one embodiment of the ratios of materials in the silicone bladder are controlled to cause the bladder to fully occlude the blood vessel in a time period of about six weeks. Also in one embodiment the blood vessel is a portosystemic shunt.

DETAILED DESCRIPTION OF THE INVENTION

In various embodiments described in enabling detail herein, the inventors provide a unique slow-occlusion apparatus to treat portosystemic shunts in animals, wherein the occlusion time period is reliably predicted and accommodated by the apparatus. The present invention is described in enabling detail using the following examples, which may describe more than one relevant embodiment falling within the scope of the present invention.

Figure 1:
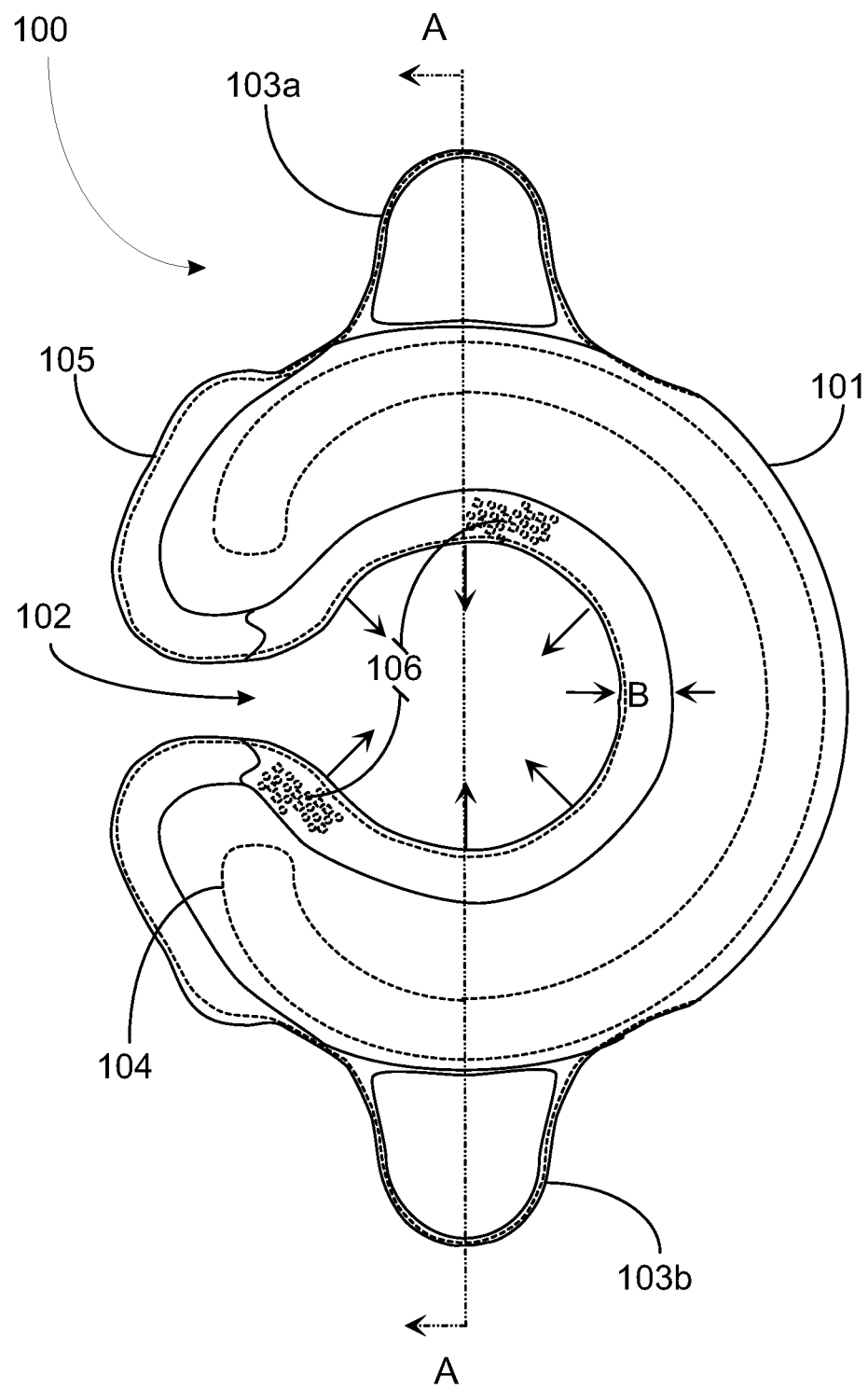
FIG. 1. is an elevation view of a silicone slow-occlusion apparatus according to an embodiment of the invention.

FIG. 1. is an elevation view of a slow-occlusion apparatus 100 according to an embodiment of the present invention. Slow-occlusion apparatus 100 may be crafted largely from medial grade silicone tubing of at least grade VI, which may be long term implantable in surgical procedures. One of the notable characteristics of the silicone is semi-permeability to water by osmosis.

Slow-occlusion apparatus 100 includes a plastic ring 104, shaped in a partial circle, encased in a silicone housing 101. Plastic ring 104 may be formed of a medical grade polyetheretherketone (PEEK) plastic. Plastic ring 104 is a rigid or semi-rigid plastic ring approximately 2 millimeters thick and 5 millimeters wide. Plastic ring 104 has a rectangular cross-section in this embodiment, and is approximately four fifths closed.

PEEK ring 104 is provided to maintain a semi-rigid structure that may prevent the occlusion apparatus from opening or widening due to the occlusion process which occurs over a period of time. The resiliency of the PEEK ring also provides for being able to open the apparatus to place the apparatus over a vessel to be occluded. In one embodiment, silicone tubing is placed over PEEK ring 104 and the tubing is closed off at both ends to encase the ring and define housing 101. Occlusion apparatus 100 in one embodiment may have approximately 6.5 millimeters outside diameter (OD) and a 5-millimeter ID lumen.

Occlusion apparatus 100 comprises a silicone bladder 105 in the form of a length of silicone tubing of a smaller diameter and wall thickness than encasement 101, cut to a length that sufficiently exceeds the circumferential length of the PEEK plastic ring. Bladder 105 is linearly attached to silicone encasement 101 around the inner diameter of encasement 101 defining a lumen region 102. The bladder tubing is fixed by adhesive to the encasement 101, forming the lumen diameter and extends out of the lumen and at least partly over the outside surface wall of encasement tubing 101. Bladder 105 may be attached to encasement 101 using a transparent or clear room-temperature-vulcanizing (RTV) silicone adhesive.

Apparatus 100 includes a pair of stirrups 103a and 103b positioned on opposite sides of the apparatus along a diameter orthogonal to a diameter passing through the gap in the apparatus. Stirrups 103a and 103b may comprise cut strips of fabric, such as Dacron fiber encased in silicone and glued in place on the outside of the occlusion apparatus, using RTV adhesive. Dacron strips provide sufficient support for manually expanding the ring using forceps or a hemostat device for placement of the occlusion apparatus over a blood vessel during a surgical implantation procedure. Other fabric and cord may be suitable. Apparatus 100 may be made translucent and radiolucent (invisible to X-rays) and may be left permanently over the occluded vessel.

Bladder 105 in one embodiment contains a mixture 106 of sodium chloride (NaCl), potassium chloride (KCl), and Polyacrylamide granules. The polyacrylamide granules swell into a hygroscopic gel like substance when exposed to moisture, and the ratio of the salt mixture changes the hygroscopic strength of the apparatus, regulating the rate of absorption of water, and therefore the time period necessary for the lumen to close. Apparatus 100 contains no metals. The salts and polymer granules are isolated within the lumen portion of bladder 105 by pinching or otherwise closing off the rest of the lumen bladder tube at the location of the gap into lumen 102.

In general operation, apparatus 100 is placed over a small blood vessel that requires occlusion. Apparatus 100 is designed to fit over small vessels such as those no larger than 5 mm or 6 mm in outside diameter. However, larger and smaller apparatus may be manufactured for use with larger or smaller vessels. The operator manipulates the apparatus by using hemostats or forceps placed in stirrups 103a and 103b to expand the apparatus against resistance of the PEEK plastic ring, enough to place it over the vessel at a place in the vessel where occlusion is desired.

Once the apparatus is placed over a vessel, the forceps is released, the PEEK ring reverts to its original diameter, and the operator may close the surgery wound and leave the apparatus isolated in the patient. In the example of FIG. 1, bladder 105 is at rest and not inflated due to moisture osmosis. The original thickness B of the bladder may be approximately 1 to 2 or 3 millimeters. As the apparatus begins to take on surrounding moisture into the bladder section through osmosis through silicone walls, the bladder begins to swell as the polyacrylamide granules transform into hygroscopic gel. The swelling of the bladder lining within the lumen of the apparatus is constrained to close the lumen against the resistance of the PEEK ring. The lumen closes the blood vessel slowly over a considerable period of time (6 weeks) to prevent potential portal hypertension.

Figure 2:
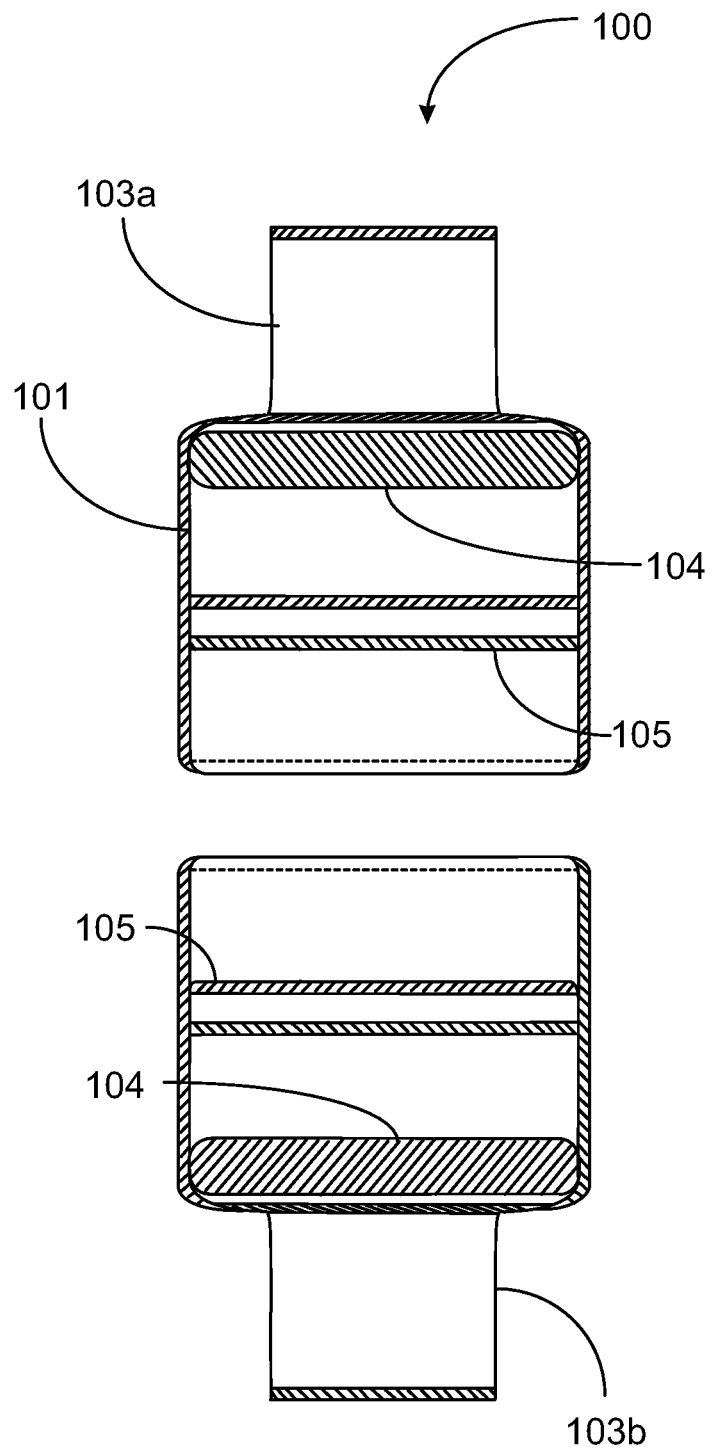
FIG. 2 is a sectioned view of the slow-occlusion apparatus of FIG. 1 taken along section line A-A.

FIG. 2 is a sectioned view of slow-occlusion apparatus 100 of FIG. 1 taken along section line A-A. Apparatus 100 is seen in section view from a center line perspective depicting Dacron stirrups 103a and 103b at opposite side of the apparatus, orthogonal to the direction of the gap into the lumen region of the apparatus. Each stirrup may be approximately 2 to 4 millimeters wide and perhaps a millimeter or less in thickness, although these dimensions may vary in alternative embodiments. The openings formed through hemostat stirrups 103a and 103b are sufficiently large to enable use of hemostats or forceps to handle the apparatus and to spread the apparatus to apply over a vessel to be occluded.

Dacron is favored by the inventor in a preferred embodiment for stirrups 103a and 103b because of its inherent strength, however other materials might be used in substitution therefor without departing from the spirit and scope of the present invention. The Dacron strips are sufficiently long as to leave enough material at either end of the stirrup to glue down to the outside of the silicon encasement 101. PEEK ring 104 provides a semi-rigid annular structure functioning as a backbone support to prevent the apparatus from opening when bladder 105 is expanding toward the center of the apparatus against the blood vessel outer wall. However, PEEK ring 104 is sufficiently flexible such that the ring may be expanded by hemostat or forceps used in conjunction with stirrups 103a and 103b to put the apparatus in place around a blood vessel.

Encasement tubing 101 completely encloses PEEK ring 104 and may be completely hollowed apart from wall thickness. In one embodiment, rectangular tubing may be used to enclose PEEK ring 104. The silicone tubing may have a consistent wall thickness such as with annular or elliptical tubing or a variable wall thickness as might be the case with some rectangular tubing. Bladder 105 has a footprint that extends significantly across the width of occlusion apparatus 100 in this example. In another embodiment, bladder 105 may be a small diameter annular or elliptical tubing that may occupy a smaller footprint than a rectangular tubing may occupy.

Figure 3:
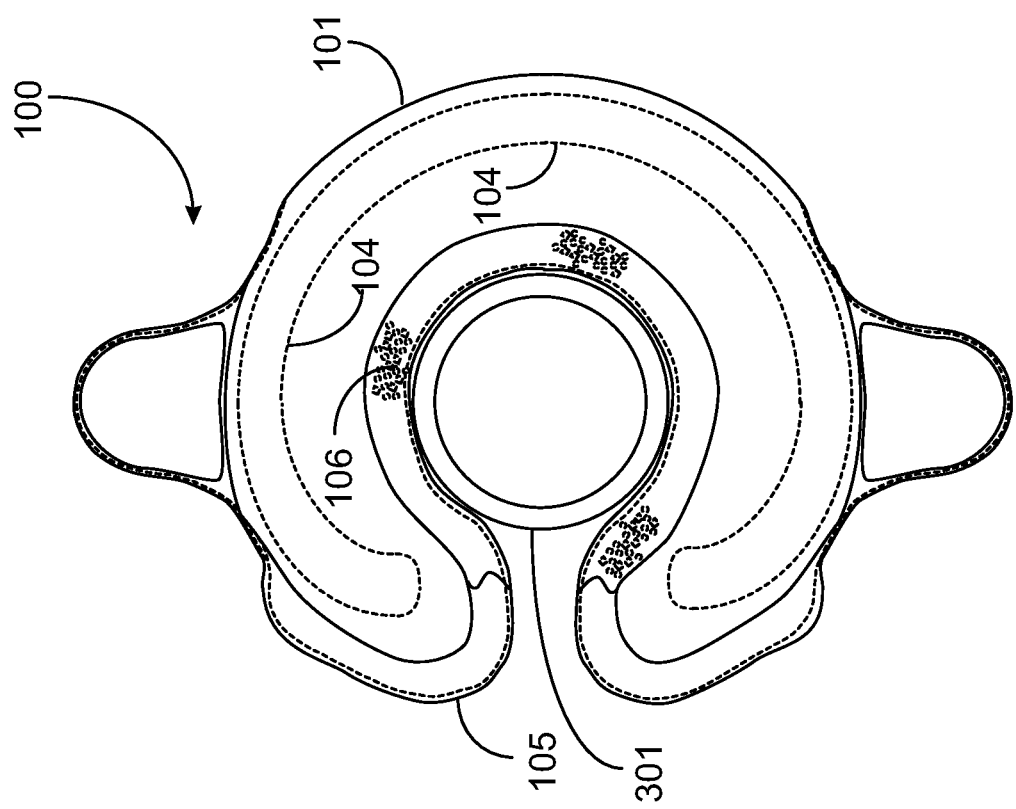
FIG. 3 is an elevation view of the slow-occlusion apparatus of FIG. 1 in an open state, positioned over a vessel to be occluded.

FIG. 3 is an elevation view of the occlusion apparatus of FIG. 1 in an open state positioned over a vessel 301 to be occluded. Forceps or a hemostat device may be used to open the apparatus and to place it over the vessel. In this example, the lumen is approximately 5 mm in diameter without expansion of bladder 105 in the lumen area. Ring 104 provides a sturdy backbone structure to prevent the apparatus from expanding or otherwise lifting off the blood vessel.

Mixture 106 is depicted within the bladder, confined to the area of the bladder occupying the lumen of the apparatus. It may be assumed that the mixture of salt and poly granules may be dispersed evenly throughout the bladder to achieve an even swelling of the bladder. However, even swelling of the bladder is not absolutely required as long as the vessel occludes properly over the time period allotted for the occlusion process to complete. The time period may be defined as the time it takes for the dry mix in the bladder to become saturated enough to begin swelling and continue to expand until the vessel is closed.

Moisture enters the bladder by osmosis through the membrane (wall) of the bladder. As the dry mixture becomes wet the polyacrylamide granules become a gel that continues to slowly expand due to continued exposure to the moisture. The rate of expansion is partly controlled by the amounts of NaCl and KCl in the mix relative to the polymer, and partly be the permeability characteristics of the silicone used.

Figure 4:
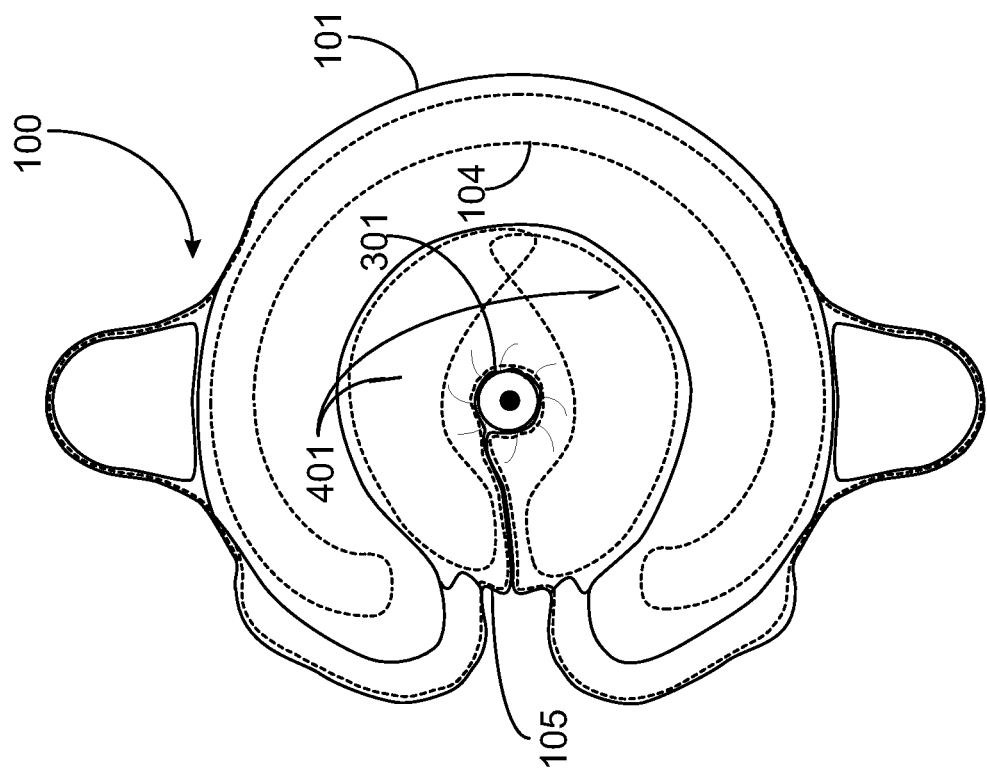
FIG. 4 is an elevation view of the occlusion apparatus of FIG. 1 in a closed (occluded) state over a vessel.

FIG. 4 is an elevation view of occlusion apparatus 100 of FIG. 1 in a closed (occluded) state over a blood vessel. Occlusion apparatus 100 is in a closed state in this example, presumably several weeks after implanted. Mixture 106 has transferred into a gel through osmosis and has continued to swell slowly. Gel 401 represents mixture 106 after about 6 weeks of absorbing water. Prior art devices occlude due to fibrosis and or thrombosis. However, these processes may vary widely relative to time in closing a vessel. The prescribed time period for occlusion in the present invention is an arbitrary 6-week period. The ratio of salts to polyacrylamide crystals in mixture (106) is key to the time period for closing the vessel and that time period may be adjusted by adjusting the ratio of the organic and inorganic salts used relative to the amount of polyacrylamide crystals.

The expansion of gel 401 causes bladder 105 to close over blood vessel 301 to the point of occlusion wherein the vessel vestiges and is eventually eliminated. Bladder 105 is closed off at the ring gap to isolate the absorbent mixture of salt and polyacrylamide into the lumen area covering the vessel. The portion of the bladder tubing extending out beyond the lumen region on either side of the encasement silicone provides support to the inflated portion of the bladder, which is the isolated section ringing the lumen.

Figure 5:
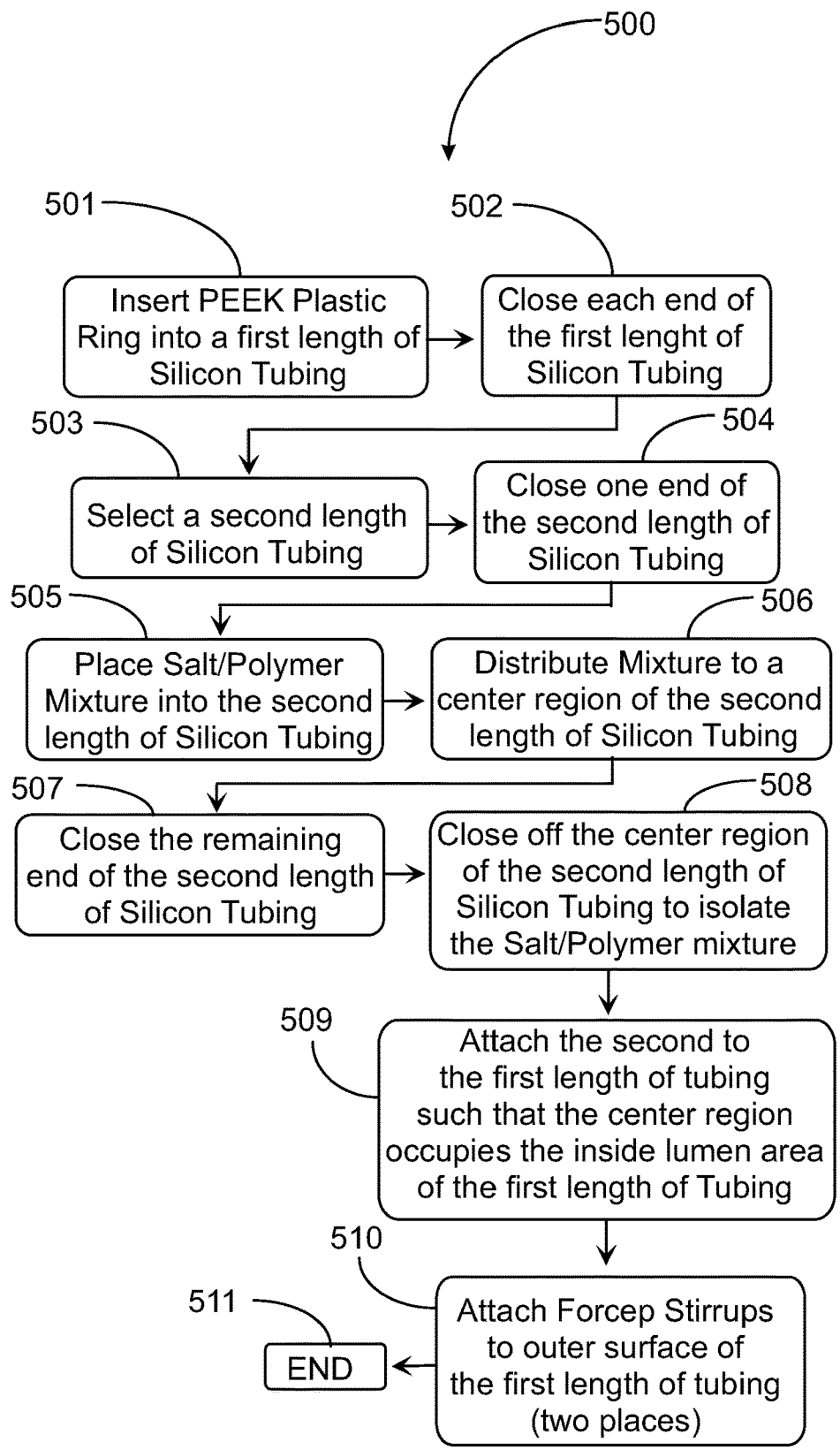
FIG. 5 is a process flow chart depicting steps for assembling the slow-occlusion apparatus of FIG. 1.

FIG. 5 is a process flow chart depicting steps for assembling the slow-occlusion apparatus of FIG. 1. At step 501 a user may insert a PEEK plastic ring analogous to ring 104 of FIG. 1 into a first length of silicone tubing. The silicone tubing may be rectangular, annular, oblong, or elliptical without departing from the spirit and scope of the present invention. The length of the silicone tubing is greater than the length of the plastic ring. At step 502 the user may close each end of the first length of the silicone tubing such as by using an RTV adhesive. At step 503, the user may select a second length of silicone tubing to form a bladder piece. The second length of tubing is significantly longer than the inside diameter of the first length of tubing installed over the plastic ring in step 501 and 502, such that the ends extend out of the lumen and over the outside surface of the encasement silicone, which is the first length of tubing.

It is noted herein that the second length of tubing is significantly smaller in diameter or height and width (rectangular) than the first length of tubing, however the selected size must be able to expand toward center point of the lumen such that the vessel will eventually be occluded. At step 504, the user may close one end of the second length of silicon tubing.

At step 505, the user may place a specified ratio and amount of a slat/polymer mixture, more particularly, NaCl/KCl/Polyacrylamide granules into the second length of tubing through the open end. At step 506, the user may distribute or otherwise dispose the mixture to a marked center region of the second length of tubing that would be sufficiently long enough to cover the lumen of the apparatus. At step 507 the user may close the remaining open end of the second length of tubing. At step 508 the user may close off or pinch to close the center region at its marked boundaries to isolate the mixture in the center section of the second length of silicone tubing.

It may be noted herein that in one aspect the user may first close the second length of tubing at a first boundary of a center section, may insert the mixture through the end having access to the center section, and then close off the second boundary of the center section of the tubing. At this point the user may then close both ends of the second length of tubing.

At step 509, the user may attach the second length of silicone tubing to the first length of silicone tubing such that the center section or region containing the salt/polymer mix occupies the inside lumen area of the first length of tubing. An RTV glue may be used to attach the bladder (second length). The user may attach the forceps stirrups or seats to the outer surface of the first length of tubing at two places (stirrups) disposed opposite of one another with the alignment thereof roughly orthogonal to the horizontal center line of the ring gap.

It will be apparent to one with skill in the art that the slow-occlusion apparatus of the invention may be provided using some or all of the described features and components without departing from the spirit and scope of the invention. It will also be apparent to the skilled person that the embodiments described above are specific examples of a single broader invention that may have greater scope than any of the singular descriptions taught. There may be many alterations made in the descriptions without departing from the spirit and scope of the present invention. The invention is limited only by the breadth of the claims below.

The invention claimed is:
1. An occlusion apparatus, comprising:
a semi-rigid, semi-circular plastic ring, having an opening at one point of circumference, fully encased in silicone material, having an outside diameter and leaving a circular, central opening of a first inside diameter;
a silicone bladder formed on the first inside diameter of the circular, central opening, from the open point on the circumference, back to the open point in the circumference, providing a hollow semi-circular silicone ring, leaving a central opening of a second inside diameter;
a mixture of sodium and potassium salts and polyacrylamide granules at a specific ratio of materials, the mixture fully enclosed in the silicone bladder; and
two stirrups, one affixed on one side of the outside diameter of the encased plastic ring, and the other opposite the first along a diameter at a right angle to a diameter passing through the opening at the one point of the circumference of the encased plastic ring;

wherein the stirrups and the opening at one point of circumference provide for spreading the apparatus by the stirrups to place the apparatus over a blood vessel, releasing the apparatus enclosing the blood vessel in the second inside diameter of the bladder, and wherein water passing through walls of the silicone bladder forms a hygroscopic gel that expands over time with further absorption of water, closing the second inside diameter of the silicone bladder, slowly occluding the blood vessel.

2. The occlusion apparatus of claim 1 wherein the ratios of materials in the silicone bladder are controlled to cause the bladder to fully occlude a blood vessel in a time period of about six weeks.

3. The occlusion apparatus of claim 1 wherein the stirrups are formed of a fabric material, coated fully in silicone, and are mounted to the encased plastic ring by a silicone adhesive.

4. The occlusion apparatus of claim 1 wherein the plastic ring is formed of medical grade polyetheretherketone (PEEK), and has a rectangular cross section.

5. The occlusion apparatus of claim 4 wherein the first inside diameter is about 5 millimeters.

6. The occlusion apparatus of claim 1 wherein the bladder is joined to the inside diameter of the encased plastic ring by a silicone adhesive.

* * * * *